(12) United States Patent
Fugger et al.

(10) Patent No.: US 8,618,113 B2
(45) Date of Patent: Dec. 31, 2013

(54) TREATMENT FOR DEMYELINATING DISEASE

(75) Inventors: Lars Fugger, Oxford (GB); Manuel Friese, Oxford (GB)

(73) Assignee: Medical Research Council (GB)

( * ) Notice: Subject to any disclaimer, the term of this patent is extended or adjusted under 35 U.S.C. 154(b) by 11 days.

(21) Appl. No.: 12/373,668

(22) PCT Filed: Jul. 16, 2007

(86) PCT No.: PCT/GB2007/002667
§ 371 (c)(1),
(2), (4) Date: Jan. 13, 2009

(87) PCT Pub. No.: WO2008/007131
PCT Pub. Date: Jan. 17, 2008

(65) Prior Publication Data
US 2010/0015127 A1 Jan. 21, 2010

Related U.S. Application Data

(60) Provisional application No. 60/830,681, filed on Jul. 14, 2006.

(30) Foreign Application Priority Data

Jul. 14, 2006 (GB) .................................. 0614058.6

(51) Int. Cl.
*A61K 31/505* (2006.01)
(52) U.S. Cl.
USPC ......................................... 514/259.1; 514/81

(58) Field of Classification Search
None
See application file for complete search history.

(56) References Cited

U.S. PATENT DOCUMENTS

2003/0219858 A1  11/2003  Seguela et al.

FOREIGN PATENT DOCUMENTS

| WO | WO 95/27510 | 10/1995 |
| WO | WO 01/52860 | 7/2001 |
| WO | WO 2006/038070 | 4/2006 |
| WO | WO 2007/059608 | 5/2007 |

OTHER PUBLICATIONS

Friese et al., Acid-sensing ion channel-1 contributes to axonal degeneration in autoimmune inflammation of the central nervous system, Dec. 2007, Nature Medicine 13(12):1483-1489.*

't Hart et al., Modelling of multiple sclerosis: lessons learned in a non-human primate, Oct. 2004, The Lancet Neurology 3(10):588-597.*

Wekerle et al., Animal Models of Multiple Sclerosis, 2006, Drug Discovery Today: Disease Models 3(4):359-367.*

* cited by examiner

*Primary Examiner* — John Ulm
(74) *Attorney, Agent, or Firm* — Klarquist Sparkman, LLP

(57) ABSTRACT

The invention relates to a method of treatment or prophylaxis of demyelinating disease, in particular the neurodegenerative phase of demyelinating disease, which comprises administration of an acid sensing ion channel (ASIC) antagonist. The invention also relates to a pharmaceutical composition comprising an ASIC antagonist in combination with an additional therapeutic agent, in particular an anti-inflammatory or immunmodulatory agent.

5 Claims, 9 Drawing Sheets

```
SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
ctgtaccatg ctggggaact                                                 20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
ctccccacac aggcaagtat                                                 20

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
gaggcgctca attacgagac                                                 20

<210> SEQ ID NO 4
<211> LENGTH: 20
<212> TYPE: DNA
```

```
<213> ORGANISM: Artificial Sequence
<220> FEATURE:
<223> OTHER INFORMATION: Synthetic oligonucleotide

<400> SEQUENCE: 4
ctgatggttt cggagtggtt                                                   20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
tgagagccac cagcttacct                                                   20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
acatgtcctc aagggagtgg                                                   20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
gatgcaaaac ccaaggagaa                                                   20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
gattggccag gtggaagata                                                   20

<210> SEQ ID NO 9
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 9
accaactggg acgacatgga gaaa                                              24

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 10
agcttctcct taatgtcacg cacg                                              24
```

TREATMENT FOR DEMYELINATING DISEASE

CROSS REFERENCE TO RELATED APPLICATIONS

This is the U.S. National Stage of International Application No. PCT/GB2007/002667, filed Jul. 16, 2007, which was published in English under PCT Article 21(2), which in turn claims the benefit of U.S. Provisional Application No. 60/830,681, filed Jul. 14, 2006 and GB Application No. 0614058.6, filed Jul. 14, 2006. All these applications are incorporated herein in their entirety.

FIELD OF THE INVENTION

The invention relates to a method of treatment or prophylaxis of demyelinating disease, in particular the neurodegenerative phase of demyelinating disease, which comprises administration of an acid sensing ion channel (ASIC) receptor antagonist. The invention also relates to a pharmaceutical composition comprising an ASIC receptor antagonist in combination with an additional therapeutic agent, in particular an anti-inflammatory or immunmodulatory agent.

BACKGROUND OF THE INVENTION

Multiple sclerosis (MS) is a chronic inflammatory disease of the white and grey matter of the central nervous system (CNS). People with MS have patches of damage in the CNS. This damage, in the form of plaques or lesions, can result in partial or occasionally, total loss of bodily functions that are controlled by areas of the CNS.

The CNS is made up of the brain and the spinal cord and contains many neurons which perform numerous functions, such as transmission of information and control of bodily functions. Neurons comprise a cell body, dendrites which are responsible for receiving information from other neurons, and axons (or nerve fibres). The importance of the axons lies in their ability to allow very weak electrical signals to travel along them; in this way, information and instructions are passed from the CNS to the body.

When looked at with the naked eye, areas where the cell bodies and dendrites are clumped together in the tissues of the CNS look grey. For this reason, they are known as 'grey matter'.

The 'white matter' includes those parts of the CNS where the axons are enclosed in myelin which is a fatty substance made up of cell membranes. This substance is wrapped many times around the axons and enables information and instructions (electrical signals or impulses) to be sent more quickly from the brain to the rest of the body, or from a particular part of the body back to the brain (Moffett D, Moffett S, Schauf C (Eds). Human Physiology, 2nd ed. Mosby-Year Book Inc; St Louis, Mo., USA, 1993).

Multiple sclerosis can run at least three clinical courses: (i) relapsing-remitting (RR) MS, which is most frequent (~85%) and characterised by discrete attacks (exacerbations) and subsequent periods of clinical stability. In most relapsing MS patients, (ii) a secondary progressive (SP) phase ensues, with continuously increasing deficits. About 10-15% of MS patients develop steadily increasing neurological deficits from onset, (iii) the primary-progressive subtype (Nosworthy et al., N Engl J Med 2000; 343, 938-952).

Multiple sclerosis typically comprises two phases: an initial inflammatory phase followed by a neurodegenerative phase.

The brain and the nervous system are nourished by capillaries and are protected by the blood-brain barrier which is an envelope of tightly packed cells that permits only oxygen and nutrients passing over from the blood (Haslet C, Chivers E R, Boon N A et al (Eds). Davidson's Principles and Practice of Medicine, 19th ed. Churchill Livingstone; Edinburgh: 2002). Sometimes this barrier breaks down and other molecules, such as antibodies and even cells, can cross the barrier. T-cells are key members of the body's immune system and it is generally accepted that the inflammatory phase of MS is caused by abnormally functioning myelin-specific CD4+ T helper 1 (TH1) cells leaking out of the blood vessels and causing swelling and damage (inflammation) in the white matter (myelin) (Hafler, D. A. et al., Immunol Rev 2005; 204, 208-231; Sospedra, M. and Martin, R., Annu Rev Immunol 2005; 23, 683-747).

The T-cells also produce chemicals which attack and break down the myelin sheath of the axons. Both the myelin and the cells that produce myelin are attacked (Noseworthy J H et al., Multiple sclerosis. New Eng J Med 2000; 343: 938-952). This process is an example of an 'autoimmune reaction'. When this 'demyelination' (i.e. damage to the myelin) happens, the passage of information and instructions through electrical signals that travel along the axons is inhibited. When the damage becomes significant, people with MS experience typical symptoms: poor muscle coordination, numbness or tingling, weakness and fatigue and other problems.

Once the inflammation phase of MS subsides, cells within the CNS begin to repair the damaged myelin. This process is called 'remyelination,' or restoration of the myelin. This cycle of damage and recovery occurs repeatedly in the myelin, often unnoticed, especially in the early stages of the disease. When, and to what extent, symptoms become apparent depends on the location, extent and severity of inflammation. If the inflammation occurs repeatedly in the same place, the repair processes may not be able to 'keep up', and permanent damage to the axons may occur which triggers the neurodegenerative phase (Steinman Nature Immunology 2, 762-764 (2001).

The signs and symptoms of MS are variable, but can include numbness, pain, pins and needles, muscle weakness or spasms, blurred vision, and fatigue, inter alia. For some people, MS episodes can be unpredictable and will include periods of relapse and remission. For others, the disease can be progressive.

MS is the commonest neurological disease of young adults, afflicting at least one million people between 17 and 65 years of age worldwide (Kantarci, O and Wingerchuk, D, Curr Opin Neurol 2006, 19:248-254.). The onset of MS will typically occur between the ages of 20 and 40 and generally affects twice as many women as men (Kantarci, O and Wingerchuk, D, Curr Opin Neurol 2006, 19:248-254.)

MS is a lifelong disease. Although no cure exists as yet, there are treatments that have been shown to reduce relapses—and some slow the progression of disability and are often called disease-modifying treatments, such as interferon beta (IFN-β), mitroxantrone and glatiramer acetate.

Another group of compounds, called corticosteroids, have also been used to control some of the symptoms of relapse in people with MS.

Thus, there is an ongoing need to find alternative and effective treatments for multiple sclerosis and other demyelinating diseases.

SUMMARY OF THE INVENTION

The present inventors have shown that administration of an acid sensing ion channel (ASIC) receptor antagonist reduces neurodegenerative deficits associated with the neurodegenerative phase of multiple sclerosis and other demyelinating diseases.

Accordingly, a first aspect of the present invention provides a method of treatment or prophylaxis of a patient suffering from demyelinating disease, comprising administering to said patient a therapeutically effective amount of an acid sensing ion channel (ASIC) receptor antagonist.

A second aspect of the present invention relates to an ASIC receptor antagonist for use in the treatment or prophylaxis of demyelinating disease.

A third aspect of the present invention provides a method of reducing axonal degeneration in a patient suffering from demyelinating disease, comprising administering to said patient a therapeutically effective amount of an acid sensing ion channel (ASIC) receptor antagonist.

In the above aspects, the ASIC receptor antagonist may be in the form of a pharmaceutical composition, additionally comprising a pharmaceutically acceptable excipient.

A third aspect of the present invention provides the use of an ASIC receptor antagonist in the manufacture of a medicament for the treatment or prophylaxis of demyelinating disease.

A fourth aspect of the present invention provides the use of an ASIC receptor antagonist in the manufacture of a medicament for the reduction or prevention of axonal degeneration in an individual suffering from a demyelinating disease.

It is preferred in all of the above aspects that the demyelinating disease is multiple sclerosis.

It is more preferred in the above aspects that it is the neurodegenerative phase of is multiple sclerosis that is treated.

In the above aspects, the ASIC receptor antagonist may be combined with an additional therapeutic agent, in particular an anti-inflammatory or immunmodulatory agent.

The invention further provides a pharmaceutical composition comprising an ASIC receptor antagonist in combination with an additional therapeutic agent, in particular an anti-inflammatory or immunmodulatory agent, and further comprising a pharmaceutically acceptable excipient. The invention also provides an ASIC receptor antagonist in combination with an additional therapeutic agent, in particular an anti-inflammatory or immunmodulatory agent for use in a method of therapy.

The invention further provides a method of screening for a compound useful in the treatment of demyelinating disease or in the reduction or prevention of axonal degeneration in an individual having a demyelinating disease, comprising determining the activity of an ASIC receptor in the presence of a test compound, wherein a decrease in activity in the presence relative to the absence of the test compound is indicative that the compound is an ASIC antagonist useful in the treatment of demyelinating disease or in the reduction or prevention of axonal degeneration in an individual having a demyelinating disease.

BRIEF DESCRIPTION OF THE FIGURES

FIG. 1A shows clinical scores for groups of WT-EAE mice, ASIC1$^{KO}$-EAE and ASIC1$^{HET}$-EAE after immunization with MOG35-55, demonstrating reduced maximum disease scores and clinical deficit in ASIC1$^{KO}$-EAE mice compared with WT-EAE or ASIC1$^{HET}$-EAE mice.

FIG. 1B shows that In vitro expanded MOG-specific T cells from WT-EAE or ASIC1$^{KO}$-EAE mice adoptively transferred into naïve WT or ASIC1$^{KO}$ mice. WT or ASIC1$^{KO}$ effector T cells equivalently provoked EAE in WT hosts (n=5 per group), while disease showed a milder course in ASIC1$^{KO}$ hosts, regardless of the origin of effector T cells, WT or ASIC1$^{KO}$. These results indicate that the ASIC1 deletion results in a neuroprotective effect without affecting T cell function.

FIGS. 7A, 7B and 7C show clinical scores for groups of amiloride-treated (started at day 5 p.i. (FIG. 7A) or day 15 p.i (FIG. 7B)) or untreated WT-EAE mice or amiloride-treated (started at day 5 p.i.) or untreated ASIC1$^{KO}$-EAE after immunization with MOG35-55 (FIG. 7C). Results are presented as mean values±s.e.m., * P<0.05

SEQUENCE LISTING

Figure 1:
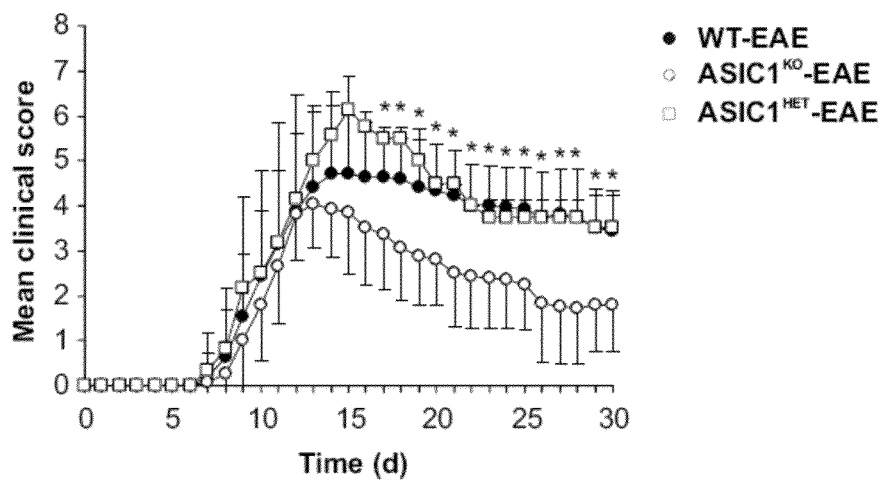
FIG. 1 shows that ASIC1$^{KO}$ ameliorates disease severity in EAE mice.
Figure 1:
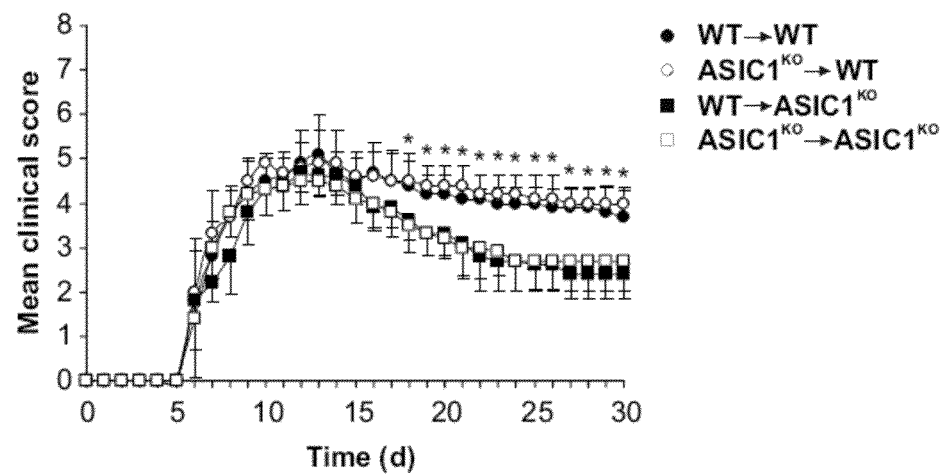

The nucleic acid sequences listed in the accompanying sequence listing are shown using standard letter abbreviations for nucleotide bases, and three letter code for amino acids, as defined in 37 C.F.R. §1.822. The Sequence Listing is submitted as an ASCII text file named 82488_Sequences, created on Aug. 20, 2011, ~4 KB, which is incorporated by reference herein.

DETAILED DESCRIPTION OF THE INVENTION

Acid-sensing ion channels (ASICs) are part of a large family that includes epithelial Na+ channels and degenerins which have been shown to be expressed ubiquitously in the mammalian nervous system, both at the periphery and in the brain (Krishtal, O. Trends in Neurosciences 2003, 26:477-483). ASICs have been found to be blocked by the presence of Ca2+ ions at a high-affinity binding site on the extracellular side of the ASIC pore. The presence of H+ or lactate has been shown to speed the release of Ca2+ ions from this binding site and therefore relieves blockade of the ASIC channel to allow Na+ currents (Immke, D. C. and McCleskey, E. W., 2003, Neuron, 37, 75-84). However, in addition to being selective for Na+, ASIC1a channels are also permeable to Ca2+ ions (Waldmann, R, et al. Nature 1997, 386:173-177.).

The identification of ASICs has been found by a number of different groups and therefore nomenclature is not consistent. For example, ASICs have also been referred to as BNaC or BNC (brain Na+ channel), DRASIC (dorsal root ASIC), MDEG (mammalian degenerin) or SPASIC (spinal cord ASIC) (Krishtal, O. Trends in Neurosciences 2003, 26:477-483). Therefore, it will be appreciated that each of these terms may interchangeably be used to refer to ASICs.

Thus far, a number of different ASICs have been identified. For example, the ASIC family has been found to comprise 6 discrete ASIC subunits: ASIC1 which has isoforms ASIC1a (amino acid sequence database entry NP_064423.2 GI:21536351) and ASIC1b (NP_001086.2 GI:21536349) (also known as ASICα or BNaC2α and ASICβ or BNaC2β, respectively), ASIC2 which has isoforms ASIC2a (NP_899233.1 GI:34452695) and ASIC2b (NP_001085.2 GI:9998944) (also known as MDEG1, BNaC1α or BNC1 and MDEG2 or BNAC1β, respectively), ASIC3 (NP_004760.1 GI:4757710) (also known as DRASIC or TNaC) and ASIC4 (NP_898843.1 GI:33942102) (also known as SPASIC).

In one embodiment, the ASIC receptor antagonist is an ASIC1a receptor antagonist.

The ASIC3 receptor is expressed mostly in the brain (Krishtal, O. Trends in Neurosciences 2003, 26:477-483)). In an alternative embodiment, the ASIC receptor antagonist is an ASIC3 receptor antagonist. The ASIC3 receptor is believed to be the most H+ sensitive of all isoforms and opens when the pH drops from 7.4 to 7.0 (Immke, D. C. and McCleskey, E. W., 2003, Neuron, 37, 75-84).

In the above embodiments, it is preferred that the ASIC antagonist is selective for the isoform concerned, i.e. that it antagonises the isoform concerned more strongly that the other ASIC isoforms. ASIC antagonism can be measured by the following method: COS cells transfected with ASIC1a, ASIC2a, ASIC3 or a combination of the subunits are voltage clamped at 260 mV and subjected to a pH drop. Inhibition of the antagonist at different compound concentrations and pH can be measured and the IC50 value determined. Selectivity is defined by a ten times greater inhibition of one ASIC1a or ASIC3 transfected cells in comparison with the cells transfected with the other subunits. (Escoubas P. et al. J Biol. Chem. 2000, 275, 25116-25121; Diochet S. et al. EMBO. 2004, 23, 1516-1525.).

It will be appreciated that an ASIC antagonist is any such agent capable of antagonising, inhibiting, blocking or downregulating the ASIC receptor.

An ASIC receptor antagonist may have no effect on the level of amyloid precursor protein (APP) in brain or other neural cells of the individual to whom it is administered, and, in particular, may not decrease or reduce over-expression or increased synthesis of APP.

An ASIC receptor antagonist may have no effect on immune or inflammatory responses in the individual. For example, administration of the ASIC receptor antagonist may have no effect on the expression of TNF or display any other immunomodulatory, immunosuppressive or anti-inflammatory effects.

The term "ASIC antagonist" as used herein, covers pharmaceutically acceptable salts and solvates of these compounds.

In one embodiment, the ASIC receptor antagonist comprises 3,5-diamino-N-(aminoiminomethyl)-6-chloropyrazinecarboxamide (amiloride, CAS registry number 2609-46-3; compound of formula (I)):

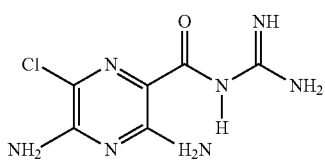
(I)

An example of a pharmaceutically acceptable salt and solvate thereof is amiloride hydrochloride dihydrate.

In an alternative embodiment, the ASIC receptor antagonist comprises a compound disclosed in WO 2006/038070 and US 2006/0079529 (both in the name of PainCeptor Pharma Corp), which are herein incorporated by reference.

In an alternative embodiment, the ASIC receptor antagonist comprises tarantula psalmotoxin which is known to specifically block ASIC1a (Krishtal, O. Trends in Neurosciences 26(9), September 2003).

In an alternative embodiment, the ASIC receptor antagonist comprises an antibody which specifically binds to the ASIC receptor.

Suitable antibodies may bind to an ASIC receptor on the mammalian cell surface and show substantially no binding to other molecules displayed on the mammalian cell surface. In some preferred embodiments, an antibody may bind to a particular ASIC receptor isoform described above and show substantially no binding to other isoforms. Suitable polyclonal and monoclonal antibodies to an ASIC receptor may be obtained using techniques which are standard in the art, including, for example immunising a mammal with a suitable peptide, such as a fragment of an ASIC receptor, or isolating a specific antibody from a recombinantly produced library of expressed immunoglobulin variable domains, e.g. using lambda bacteriophage or filamentous bacteriophage which display functional immunoglobulin binding domains on their surfaces; for instance see WO92/01047.

Preferred antibodies may be chimeric, humanised or human antibodies and may be whole antibodies or antibody fragments such as scFvs, Fabs or dAbs.

In an alternative embodiment, the ASIC receptor antagonist comprises a sense or anti-sense nucleic acid molecule which specifically down-regulates expression of the ASIC receptor.

For instance, expression of an ASIC receptor gene may be inhibited using anti-sense or RNAi technology. The use of these approaches to down-regulate gene expression is now well-established in the art.

Suitable sense or anti-sense nucleic acid molecule which specifically down-regulate expression of the ASIC receptor may be designed using routine techniques from the known coding sequence of the ASIC receptor.

Anti-sense oligonucleotides may be designed to hybridise to the complementary sequence of nucleic acid, pre-mRNA or mature mRNA, interfering with the production of polypeptide so that its expression is reduced or completely or substantially completely prevented. In addition to targeting coding sequence, antisense techniques may be used to target control sequences of a gene, e.g. in the 5' flanking sequence, whereby the antisense oligonucleotides can interfere with expression control sequences. The construction of antisense sequences and their use is described for example in Peyman and Ulman, Chemical Reviews, 90:543-584, (1990) and Crooke, Ann. Rev. Pharmacol. Toxicol., 32:329-376, (1992).

An alternative to anti-sense is to use a copy of all or part of the target gene inserted in sense, that is the same, orientation as the target gene, to achieve reduction in expression of the target gene by co-suppression; Angell & Baulcombe (1997) The EMBO Journal 16, 12:3675-3684; and Voinnet & Baulcombe (1997) Nature 389: pg 553). Double stranded RNA (dsRNA) has been found to be even more effective in gene silencing than both sense or anti-sense strands alone (Fire A. et al Nature, Vol 391, (1998)). dsRNA mediated silencing is gene specific and is often termed RNA interference (RNAi).

RNA interference is a two-step process. First, dsRNA is cleaved within the cell to yield short interfering RNAs (siRNAs) of about 21-23 nt length with 5' terminal phosphate and 3' short overhangs (~2 nt). The siRNAs target the corresponding mRNA sequence specifically for destruction (Zamore P. D. Nature Structural Biology, 8, 9, 746-750, (2001)

RNAi may be also be efficiently induced using chemically synthesized siRNA duplexes of the same structure with 3'-overhang ends (Zamore P. D. et al Cell, 101, 25-33, (2000)). Synthetic siRNA duplexes have been shown to specifically suppress expression of endogenous and heterologous genes in a wide range of mammalian cell lines (Elbashir S M. et al. Nature, 411, 494-498, (2001)).

Oligonucleotides may be generated in vitro or ex vivo for administration or sense or anti-sense RNA may be generated in vivo within cells in which down-regulation is desired.

Another possibility is that nucleic acid is used which on transcription produces a ribozyme, able to cut nucleic acid at a specific site—thus also useful in influencing gene expression. Background references for ribozymes include Kashani-Sabet and Scanlon, 1995, Cancer Gene Therapy, 2(3): 213-223, and Mercola and Cohen, 1995, Cancer Gene Therapy, 2(1), 47-59.

In an alternative embodiment, an ASIC antagonist may be tested and identified in accordance with the screening procedures outlined in US 2003/0186860 (Welsh et al), which is herein incorporated by reference.

A demyelinating disease is a condition in which the myelin sheath which surrounds neurons in nervous tissue is lost or damaged, leading to axonal degeneration and impaired signal transduction in the affected nerves. Examples of demyelinating diseases include multiple sclerosis, transverse myelitis, Guillan-Barre syndrome, optic neuritis, neuromyelitis optica, acute disseminated encephalomyelitis, adrenoleukodystrophy, adrenomyelomeuropathy, idiopathic inflammatory demyelinating disease, central pontine myelinolysis, and progressive multifocal leukoencephalopathy.

In preferred embodiments, the demyelinating disease is multiple sclerosis.

In preferred embodiments, a demyelinating condition is not associated with over-expression or increased synthesis of amyloid precursor protein (APP) in brain or other neural cells. Individuals suitable for treatment as described herein may not have a condition associated with increased or elevated APP levels.

The ASIC receptor antagonists of the invention have been demonstrated to reduce axonal degeneration and neurodegenerative deficits associated with the neurodegenerative phase of multiple sclerosis. Therefore, ASIC antagonists of the invention may represent an effective treatment of the chronic neurodegenerative phase of multiple sclerosis and other demyelinating diseases which display distinct inflammatory and neurodegenerative phases. ASIC antagonists may, for example, reduce acidosis induced axonal degeneration in individuals having a demyelinating disease without affecting the inflammatory responses associated with the demyelinating disease.

Furthermore, in view of the fact that the neurodegenerative phase of multiple sclerosis will follow the inflammatory phase, onset of the neurodegenerative phase may be predicted (Kapoor, R., Curr Opin Neurol 2006, 19:255-259). In this manner, ASIC antagonists of the invention may, in some embodiments, constitute a prophylactic treatment for demyelinating diseases such as multiple sclerosis, in particular with respect to the neurodegenerative phase of multiple sclerosis.

An individual suitable for treatment as described herein may be identified as suffering from the neurodegenerative phase of the multiple sclerosis or other demyelinating disease which display distinct inflammatory and neurodegenerative phases. This may be carried out using routine diagnostic criteria. The neurodegenerative phase may be identified prior to the methods of treatment described herein or as part of such a method. For example, a method may comprise the step of identifying the individual as suffering from the neurodegenerative phase of multiple sclerosis or other demyelinating disease. As described above, the symptoms and underlying pathology of the neurodegenerative phase are distinct from the inflammatory phase of multiple sclerosis.

The ASIC receptor antagonists of the invention may be used in combination with other therapeutic agents, for example other medicaments claimed to be useful as suitable treatments of demyelinating disease, neurodegeneration (e.g. neuroprotective agents) or inflammation (e.g. immunomodulatory agents or immunosuppressive agents).

Examples of suitable immunomodulatory agents include interferon-beta, glatiramer acetate and statins. Examples of suitable immunosuppressive agents include mitoxantrone, natalizumab, FTY720, antagonists/antibodies to co-stimulatory molecules and cytokines/chemokines. Examples of suitable neuroprotective agents include glutamate receptor blockers, neurothrophic factors and other ion channel blockers.

When the compounds are used in combination with other therapeutic agents, the compounds may be administered either sequentially or simultaneously by any convenient route. A pharmaceutical combination comprising an ASIC receptor antagonist and an anti-inflammatory agent provides the advantage of treating the symptoms of both key phases of the demyelinating disease (e.g. the inflammatory phase and the neurodegenerative phase).

Other aspects of the invention relate to methods of screening for compounds useful in the treatment of demyelinating diseases.

A method of screening for a compound which is useful in the treatment of a demyelinating disease or useful in reducing axonal degeneration in an individual with a demyelinating disease may comprise:
a) contacting an ASIC receptor with a test compound; and
b) determining the interaction of the ASIC receptor with the test compound.

In some embodiments, the interaction of the ASIC receptor with the test compound may be determined by determining the presence or amount of binding of the test compound to the ASIC receptor. The presence of binding may be indicative that the test compound is a candidate ASIC receptor antagonist and may be useful in the treatment of a demyelinating disease. Candidate ASIC receptor antagonists may be tested for ability to inhibit the activity of an ASIC receptor, as described below.

In other embodiments, the interaction of the ASIC receptor with the test compound may be determined by determining the activity of the ASIC receptor in the presence of the test compound. A decrease in activity in the presence relative to the absence of test compound is indicative that the test compound is an ASIC receptor antagonist and may be useful in the treatment of a demyelinating disease.

ASIC receptors are described elsewhere herein. In some preferred embodiments, the ASIC receptor is an ASIC1 receptor, such as ASIC1a (NP_064423.2 GI:21536351), ASIC1b (NP_001086.2 GI:21536349), an ASIC2 receptor such as ASIC2a (NP_899233.1 GI:34452695) and ASIC2b (NP_001085.2 GI:9998944), an ASIC3 receptor (NP_004760.1 GI:4757710) or an ASIC4 receptor (NP_898843.1 GI:33942102) or a variant of any of these, as described above.

Variants of an ASIC receptor include natural allelic variants which are found in one or more individuals within a population and may differ from the reference ASIC receptor sequence by the addition, deletion, substitution and/or insertion of one or more amino acids, whilst retaining native activity. For example up to ten amino acids may differ.

A variant may retain activity of the reference ASIC receptor.

An amino acid sequence which is a variant of a reference ASIC receptor sequence may comprise a sequence which shares greater than about 40% sequence identity with the reference sequence, greater than about 50%, greater than about 60%, greater than about 70%, greater than about 80%, greater than about 90% or greater than about 95%.

Sequence similarity and identity are commonly defined with reference to the algorithm GAP (Genetics Computer Group, Madison, Wis.). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul et al. (1990) J. Mol. Biol. 215: 405-410), FASTA (which uses the method of Pearson and Lipman (1988) PNAS USA 85: 2444-2448), or the Smith-Waterman algorithm (Smith and Waterman (1981) J. Mol. Biol. 147: 195-197), or the TBLASTN program, of Altschul et al. (1990) supra, generally employing default parameters. In particular, the psi-Blast algorithm (Nucl. Acids Res. (1997) 25 3389-3402) may be used. Sequence identity and similarity may also be determined using Genomequest™ software (Gene-IT, Worcester Mass. USA).

Fragments which retain all or part of the activity of the full-length ASIC receptor may be generated and used in the methods described herein, whether in vitro or in vivo. Suitable ways of generating fragments include recombinant techniques and chemical synthesis techniques which are well known in the art.

A fragment of a full-length ASIC receptor sequence consists of fewer amino acids than the full-length sequence. For example a fragment may consist of at least 30, at least 40, at least 50, at least 60, at least 70, at least 80, at least 90 or at least 100 amino acids of the full length sequence but 200 or less, or 100 or less amino acids of the full length sequence.

An ASIC receptor for use in the present methods may be expressed on a cell surface. A method of screening for a compound useful in the treatment of a demyelinating disease may comprise:
a) contacting a cell with a test compound; and
b) determining the expression or activity of an ASIC receptor in said cell.

A reduction in the amount of expression or activity of the ASIC receptor in the cells relative to controls is indicative that the compound is useful in the treatment of a demyelinating disease. Suitable controls include cells which are not treated with the test compound.

Demyelinating diseases and ASIC receptors are discussed in more detail above.

A suitable cell may be any eukaryotic cell which expresses or is capable of expressing an ASIC receptor as described above, for example yeast, insect or mammalian cell. The ASIC receptor may be a heterologous protein encoded by nucleic acid introduced into the cell by recombinant means or may be naturally expressed by the cell.

Test compound may be contacted with the cells by supplementing the buffer or culture medium with the test compound.

The activity of an ASIC receptor in a cell may be determined by standard techniques, for example electrophysiology techniques such as voltage clamping. The precise format for performing the methods described herein may be varied by those of skill in the art using routine skill and knowledge.

Compounds which may be screened using the methods described herein may be natural or synthetic chemical compounds used in drug screening programmes. Extracts of plants, microbes or other organisms which contain several characterised or uncharacterised components may also be used.

One class of putative compounds for inhibition of ASIC receptor can be derived from the ASIC receptor itself. Peptide fragments of from 5 to 40 amino acids, for example, from 6 to 10 amino acids may be tested for their ability to disrupt ASIC receptor activity.

The inhibitory properties of a peptide fragment as described above may be increased by the addition of one of the following groups to the C terminal: chloromethyl ketone, aldehyde and boronic acid. These groups are transition state analogues for serine, cysteine and threonine proteases. The N terminus of a peptide fragment may be blocked with carbobenzyl to inhibit aminopeptidases and improve stability (Proteolytic Enzymes 2nd Ed, Edited by R. Beynon and J. Bond, Oxford University Press, 2001).

Antibodies which bind specifically to the ASIC receptor form a further class of putative agents useful in treating demyelinating diseases. Suitable antibodies are described in more detail above.

Other candidate compounds may be based on modelling the 3-dimensional structure of the ASIC receptor and using rational drug design to provide candidate compounds with particular molecular shape, size and charge characteristics. For example, a chemical compound may be modelled to resemble the three dimensional structure of the component in an area which contacts another component, and in particular the arrangement of the key amino acid residues as they appear. Techniques for the rational design of compounds that bind to target proteins are well known in the art.

An alternative approach to antagonism of an ASIC receptor employs regulation at the nucleic acid level to inhibit activity or function by down-regulating production of the ASIC receptor. Sense and anti-sense nucleic acids which down-regulate production of the ASIC receptor are described in more detail above.

Combinatorial library technology provides an efficient way of testing a potentially vast number of different compounds for ability to modulate an interaction. Such libraries and their use are known in the art, for all manner of natural products, small molecules and peptides, among others. The use of peptide libraries may be preferred in certain circumstances.

The amount of test compound or compound which may be added to a method of the invention will normally be determined by serial dilution experiments. Typically, from about 0.001 nM to 1 mM or more of test compound may be used, for example from 0.01 nM to 100 µM, e.g. 0.1 to 50 µM, such as about 10 µM.

A method may comprise identifying the test compound as a compound which reduces the activity or amount of ASIC receptor in a cell and which may be useful in the treatment of a demyelinating disease.

A test compound identified using one or more initial screens as having ability to inhibit or reduce the activity or amount of ASIC receptor in a cell, may be assessed further using one or more secondary screens. A secondary screen may, for example, involve testing for a biological function such as an effect on neurodegeneration or neurological performance, for example in an animal model of a demyelinating disease such as MS.

The test compound may be isolated and/or purified or alternatively, it may be synthesised using conventional techniques of recombinant expression or chemical synthesis. Furthermore, it may be manufactured and/or used in preparation, i.e. manufacture or formulation, of a composition such as a medicament, pharmaceutical composition or drug. These may be administered to individuals, either alone or in combination with other therapeutic agents, for the treatment of a demyelinating disease. Methods of the invention may thus comprise formulating the test compound in a pharmaceutical composition with a pharmaceutically acceptable excipient, vehicle or carrier for therapeutic application, as discussed further below.

Following identification of a compound which increases the amount or activity of an ASIC receptor in a cell, and which may therefore be useful in the treatment of a demyelinating disease, a method may further comprise modifying the compound to optimise the pharmaceutical properties thereof.

The modification of a 'lead' compound identified as biologically active is a known approach to the development of pharmaceuticals and may be desirable where the active compound is difficult or expensive to synthesise or where it is unsuitable for a particular method of administration, e.g. peptides are not well suited as active agents for oral compositions as they tend to be quickly degraded by proteases in the alimentary canal. Modification of a known active compound (for example, to produce a mimetic) may be used to avoid randomly screening large number of molecules for a target property.

Modification of a 'lead' compound to optimise its pharmaceutical properties commonly comprises several steps. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled according to its physical properties, e.g. stereochemistry, bonding, size and/or charge, using data from a range of sources, e.g. spectroscopic techniques, X-ray diffraction data and NMR.

Computational analysis, similarity mapping (which models the charge and/or volume of a pharmacophore, rather than the bonding between atoms) and other techniques can be used in this modelling process.

In a variant of this approach, the three-dimensional structure of the compound which inhibits the expression or activity of ASIC receptor in a cell is modelled. This can be especially useful where the compound changes conformation, allowing the model to take account of this in the optimisation of the lead compound.

A template molecule is then selected, onto which chemical groups that mimic the pharmacophore can be grafted. The template molecule and the chemical groups grafted on to it can conveniently be selected so that the modified compound is easy to synthesise, is likely to be pharmacologically acceptable, and does not degrade in vivo, while retaining the biological activity of the lead compound. The modified compounds found by this approach can then be screened to see whether they have the target property, or to what extent they exhibit it. Modified compounds include mimetics of the lead compound.

Further optimisation or modification can then be carried out to arrive at one or more final compounds for in vivo or clinical testing.

As described above, a compound identified and/or obtained using the present methods may be formulated into a pharmaceutical composition.

Treatment

The term "treatment", as used herein in the context of treating a condition, pertains generally to treatment and therapy in which some desired therapeutic effect is achieved, for example, the inhibition of the progress of the condition, and includes a reduction in the rate of progress, a halt in the rate of progress and amelioration of the condition, and cure of the condition.

Pharmaceutically Acceptable Salts

The term "pharmaceutically acceptable salts" as used herein refers to non-toxic salts of the ASIC receptor antagonists which are generally prepared by reacting the free base with a suitable organic or inorganic acid or by reacting the free acid with a suitable organic or inorganic base. Examples of pharmaceutically acceptable salts are discussed in Berge, et al., "Pharmaceutically Acceptable Salts", J. Pharm. Sci., 66, 1-19 (1977).

For example, if the compound is anionic, or has a functional group which may be anionic (e.g., —COOH may be —COO—), then a salt may be formed with a suitable cation. Examples of suitable inorganic cations include, but are not limited to, alkali metal ions such as Na+ and K+, alkaline earth cations such as Ca2+ and Mg2+, and other cations such as Al3+. Examples of suitable organic cations include, but are not limited to, ammonium ion (i.e., NH4+) and substituted ammonium ions (e.g., NH3R+, NH2R2+, NHR3+, NR4+). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH3)4+.

If the compound is cationic, or has a functional group which may be cationic (e.g., —NH2 may be —NH3+), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: acetic, propionic, succinic, gycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, toluenesulfonic, methanesulfonic, ethanesulfonic, ethane disulfonic, oxalic, isethionic, valeric, and gluconic. Examples of suitable polymeric anions include, but are not limited to, those derived from the following polymeric acids: tannic acid, carboxymethyl cellulose.

Other salts which are not pharmaceutically acceptable may be useful in the preparation of an ASIC receptor antagonist and these form a further aspect of the present invention.

Solvates

In addition, some of the ASIC receptor antagonists may form solvates with water or common organic solvents. Such solvates are also encompassed within the scope of the present invention. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

Pharmaceutical Compositions

The combinations referred to above may conveniently be administered alone or in combination with pharmaceutically acceptable carriers or excipients, in either single or multiple doses, sequentially or simultaneously. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy 21th Ed., Lippincott Williams & Wilkins (2005), which is incorporated herein by reference.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospho-lipids, fatty acids, fatty acid amines, polyoxyethylene and water.

Similarly, the carrier or diluent may include any sustained release material known in the art, such as glyceryl monostearate or glyceryl distearate, alone or mixed with a wax. The pharmaceutical compositions formed by combining ASIC receptor antagonists and the pharmaceutically acceptable carriers are then readily administered in a variety of dosage forms suitable for the disclosed routes of administration. The formulations may conveniently be presented in unit dosage form by methods known in the art of pharmacy.

A pharmaceutical composition of the invention, which may be prepared by admixture, suitably at ambient temperature and atmospheric pressure, may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

For topical use, sprays, creams, ointments, jellies, gels, inhalants, dermal patches, implants, solutions of suspensions, etc., containing the compounds of the present invention are contemplated. For the purpose of this application, topical applications shall include mouth washes and gargles.

The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

Pharmaceutical compositions for oral administration include solid dosage forms such as hard or soft capsules, tablets, troches, dragees, pills, lozenges, powders and granules and liquid dosage forms for oral administration include solutions, emulsions, aqueous or oily suspensions, syrups and elixirs, each containing a predetermined amount of the active ingredient, and which may include a suitable excipient.

Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations.

Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc.

The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectible aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art. Depot injectable formulations are also contemplated as being within the scope of the present invention.

The compositions for rectal administration of the compounds may also be in the form of suppositories. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

The pharmaceutical composition may contain from 0.1% to 99% by weight, preferably from 10 to 60% by weight, of the active material, depending on the method of administration.

Dosage

A typical oral dosage is in the range of from about 0.05 to about 1000 mg, preferably from about 0.1 to about 500 mg, and more preferred from about 1.0 mg to about 200 mg administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

For parenteral routes such as intravenous, intrathecal, intramuscular and similar administration, typically doses are in the order of about half the dose employed for oral administration.

An ASIC receptor antagonist or a pharmaceutically acceptable salt, solvate or prodrug thereof may be administered in an amount sufficient to elicit a neuroprotective effect as described herein but insufficient to elicit an immunmodulatory effect or alter TNF expression levels.

When an ASIC receptor antagonist or a pharmaceutically acceptable salt, solvate or prodrug thereof is used in combination with a second therapeutic agent active against the same disease state the dose of each compound may differ from that when the compound is used alone. Appropriate doses will be readily appreciated by those skilled in the art.

The invention will be further illustrated by the following non-limiting examples.

EXAMPLES

Mice, Induction and Assessment of EAE 6-10 week old female and male C57BL/6 mice, ASIC1 HET or ASIC1KO028 mice were immunized subcutaneously in the flank with 200 µg MOG35-55 emulsified in complete Freund's adjuvant (CFA; Sigma-Aldrich) supplemented with 4 mg/ml *M. tuberculosis* H37Ra (Difco). 200 ng pertussis toxin (PT; Sigma-Aldrich) was administered intravenously on the day of immunization and 2 days later. The mice were sex matched among the different groups. Mice were treated with 5 mg/kg body weight amiloride (Sigma-Aldrich) i.p., administered in 100 µl daily starting from 5 or 15 days after immunization or with the same volume of PBS. No significant difference was observed between untreated and PBS-treated WT-EAE (data not shown) and data from these groups were pooled (WT-EAE). The mice were then monitored for clinical and neurological deficits and scored as previously described29. For adoptive transfer of MOG-reactive T cells, C57BL/6 WT or ASIC1KO mice were immunized as described above. Ten days later, a single cell suspension was prepared from draining lymph nodes, and cells were cultured in the presence of 10 µg of MOG35-55 and 5 U/ml recombinant human IL-2 (Becton Dickenson) in RPMI 1640 with 10% FCS, 100 U/ml penicillin, and 100 µg/ml streptomycin (Invitrogen). After 4 days non-adherent T cells were collected by centrifugation on Histopaque 1088 (Sigma-Aldrich), and 1×10⁷ T cells were injected i.v. into naïve WT or ASIC1KO recipient mice. Each mouse also received 200 ng of PT on days 0 and 2 after transfer. All experiments detailed have been approved by the local ethics committee and have been licensed under the Animals Scientific Procedures Act of the UK Home Office.

Tissue Processing and Immunocytochemistry

Mice were anesthetized with Hypnovel/Hypnorm/water (1:1:2; 0.1 ml/10 g, i.p) mixture and perfused with 4% paraformaldehyde in 0.14 M phosphate buffer. Optic nerves and spinal cord were carefully excised and postfixed for 30 min, rinsed in PBS and cryoprotected in 30% sucrose in PBS overnight. To standardize the site of analysis of spinal cord the cervical enlargement was identified and transected midpoint. Transverse cryosections (12 µm) of mid-cervical spinal cord or optic nerve were placed onto slides, desiccated overnight and processed for immunocytochemistry. Briefly, sections were incubated in blocking solution (PBS containing 5% normal goat serum and 1% BSA) containing 0.1% Triton X-100 and 0.02% sodium azide at room temperature for 30 min. Sections were then incubated simultaneously or in combination with antibodies to phosphorylated (SMI 31, 1:1000; Covance), non-phosphorylated neurofilaments (SMI 32, 1:1000; Covance), anti-CD45 rat IgG (1:100; Caltag Laboratories), anti-CD3 hamster IgG (1:100; Caltag Laboratories), anti-HIF1 αrabbit IgG (1:100; Zymed Laboratories) overnight at 4° C. Secondary antibodies were goat anti-mouse IgG-Alexa Fluor 568 or Fluor 488, goat anti-rat IgG-Alexa Fluor 647 or Fluor 488, goat anti-hamster IgG-Alexa Fluor 433 and goat anti-rabbit IgG-Alexa Fluor 568 (all 1:1000 and from Molecular Probes). Control experiments with no primary antibody or secondary antibody showed no staining (data not shown). Analysis of sections was performed as described in Supplementary Methods online.

In Situ Hybridization Cytochemistry

Figure 3:
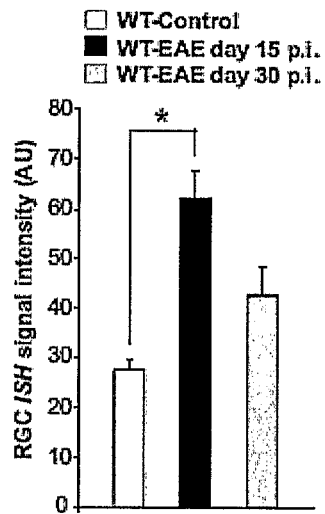
FIG. 3 shows quantification of in situ hybridization signal intensity with a specific ASIC1 probe or ASIC1 sense probe (negative control) in retinal ganglion cells (RGC) of un-immunized WT mice and mice with EAE 15 or 30 days p.i. given in arbitrary units (AU) in retinal ganglion cells (RGC).

DIG-labeled sense and antisense riboprobes recognizing ASIC1 nucleotide sequences 1091-1634 (GenBank, NM_009597.1) were prepared by in vitro transcription. Sections were processed for in situ hybridization cytochemistry as previously[30] described using an isoform-specific riboprobe to ASIC1. Sense riboprobes yielded no signals on in situ hybridization (FIG. 3). Analysis of sections was performed as described in Supplementary Methods.

Ex Vivo Optic Nerve Injury Model.

6-10 week old C57BL/6 mice or ASIC1KO mice were terminally anesthetized followed by rapid removal of eye and respective optic nerve up to the optic chiasm. Particular care was undertaken to prevent damage to the optic nerve during excision and handling. The eye (including retina) and optic nerve from C57BL/6 WT and ASIC1KO mice were incubated at 37° C. in a humidified incubator at 5% CO2 atmosphere using Leibovitz tissue culture media (Sigma-Aldrich) alone or containing either amiloride (100 µM; Sigma-Aldrich) or the venom of the tarantula Psalmopoeus cambridgei, containing PcTx (100 ng/ml; SpiderPharm). The experimental conditions of WT alone, ASIC1KO alone, WT plus amiloride and WT plus PcTx were subject to pH 7.4 (HEPES 25 mM, 14.7 mM NaHCO3) or pH 6.5 (MES 25 mM, 1.5 mM NaHCO3). Following overnight (18 h) incubation, the eye and optic nerve tissue was removed from the media and fixed in 4% paraformaldehyde in 0.14 M phosphate buffer for 30 min, cryoprotected and then flat embedding in rectangular molds in OCT medium. Tissue was sectioned and immunocytochemistry performed as described above. Analysis of sections was performed as described in Supplementary Methods.

In Vivo pH Measurement

EAE was induced in 6-10 week old C57BL/6 mice and at day 15 p.i. mice were anesthetized with Hypnovel/Hypnorm/water (1:1:2; 0.1 ml/10 g, i.p) mixture. During deep anesthesia, the spinal cord was surgically prepared by using a dissection microscope. Bleeding was stopped by electro cauterizing. A microtip pH meter (World Precision Instruments) was inserted into the spinal cord at two different locations and an average pH was measured and recorded.

RT-PCR

Murine lymph node cells, splenocytes or brain tissue was isolated from indicated mice. T and B cells were negatively separated by pan-T and pan-B cell magnetic bead kits (Miltenyi Biotec). Macrophages were isolated from murine peritoneal cavity 3 days after injection of 1 ml of 3% (w/v) thioglycollate (Sigma-Aldrich). RNA extraction and cDNA synthesis were performed by standard methods. Thermal cycler parameters were 2 min at 50° C., 10 min at 95° C., and 40 cycles of denaturation at 95° C. for 15 s followed by annealing and extension at 60° C. for 1 min. The following specific primers (forward, reverse) were used:

```
mASIC1F 5'-CTGTACCATGCTGGGGAACT-3',     (SEQ ID NO: 1)

mASIC1R 5'-CTCCCCACACAGGCAAGTAT-3';     (SEQ ID NO: 2)

mASIC2F 5'-GAGGCGCTCAATTACGAGAC-3',     (SEQ ID NO: 3)

mASIC2R 5'-CTGATGGTTTCGGAGTGGTT-3';     (SEQ ID NO: 4)

mASIC3F 5'-TGAGAGCCACCAGCTTACCT-3',     (SEQ ID NO: 5)

mASIC3R 5'-ACATGTCCTCAAGGGAGTGG-3';     (SEQ ID NO: 6)

mASIC4F 5'-GATGCAAAACCCAAGGAGAA-3',     (SEQ ID NO: 7)

mASIC4R 5'-GATTGGCCAGGTGGAAGATA-3';     (SEQ ID NO: 8)

ActinF 5'-ACCAACTGGGACGACATGGAGAAA-3', (SEQ ID NO: 9)

ActinR 5'-AGCTTCTCCTTAATGTCACGCACG-3'. (SEQ ID NO: 10)
```

Immunoblot

Cells or tissue were prepared as stated for RT-PCR and homogenized in lysis buffer (50 mM Tris-HCl (pH 8) containing 120 mM NaCl, 5 mM EDTA, 0.5% NP-40, 2 μg/ml aprotinin, 10 μg/ml leupeptin and 100 μg/ml PMSF, all from Sigma-Aldrich). Aliquots of tissue lysates were electrophoresed on 12% SDS-PAGE gels under reducing conditions and transferred to nitrocellulose (Amersham/GE Healthcare). The lysates were assessed at 20 μg total protein per lane. After blocking with 5% (w/v) dried milk in PBS for 30 min, the filters were incubated with rabbit anti-ASIC1 serum (MTY19)3 overnight at 4° C., washed and incubated with peroxidase-conjugated mouse anti-rabbit IgG (diluted 1:3000) (Sigma-Aldrich) for 3 h at RT. Labeling was visualized using enhanced chemiluminescence (ECL, Amersham).

T Cell Proliferation Assay

Cell suspensions prepared from spleens (5×105 cells/well) were plated in 100 μl RPMI 1640 medium containing 10% fetal calf serum (Sigma-Aldrich), 2 mM L-glutamine, 100 U/ml penicillin/streptomycin (Invitrogen), and MOG35-55 at indicated concentrations (recall assays) or with anti-CD3/-CD28 antibody coated beads (Dynal) (in vitro proliferation assays). Control wells contained responder splenocytes plus medium alone. All conditions were measured in triplicate wells. During the last 18 h of the 4 day culture period, cultures were pulsed with 1 μCi/well [methyl-3H]-thymidine (Amersham/GE Healthcare). Cells were harvested (Tomtec, Hamden, Conn.) and incorporated radioactivity was determined in a Wallac 1450 Microbeta Plus Liquid Scintillation Counter.

Flow Cytometry

Antibodies used for flow cytometry analysis. Anti-mouse CD3 (145-2C11), CD4 (L3T4), CD8 (53-6.7), CD11b (M1/70), CD11c (HL3), NK1.1 (PK136), CD40 (3/23), CD80 (16-10A1), CD86 (GL1), I-Ak (10-3.6), I-A/I-E (M5/114.15.2) (all from Becton Dickenson) and CD19 (6D5; Serotec). Analysis was done by using a Cyan ADP (Dako).

Tissue Analysis

For analysis of sections, multiple representative images were accrued with a confocal microscope (Radiance 2000; Bio-Rad Laboratories) system on a microscope (BX51; Olympus). 2-4 blinded images per animal were taken of the dorsal corticospinal tract (n=5 per group, 93,897 total axons), dorsal column (n=5 per group, 13,046 total axons) and optic nerve (n=5 per group in vivo, 56,979 total axons; n=4-5 per group in vitro, 213,068 total axons) through a 100× objective (UplanF1; Olympus), with a 2× digital zoom using Lasersharp software (Bio-Rad Laboratories). Quantification of axonal profiles was performed utilizing ImageJ and adapted ICTN plugin which counted axonal profiles based on a minimum diameter of the axon, separation and threshold intensity with values fixed across experimental groups for each type of tissue examined. Accuracy of automated counting technique was confirmed by manual counting of sample images (2,400 axons approx.) with <2% non significant difference (P=0.89) in the number of axons between a blinded observer and automated counting technique. Moreover, estimates of the total numbers of axons in WT controls of optic nerve (42,000 per optic nerve) and corticospinal tract (25,000 per unilateral dorsal corticospinal tract) by ImageJ/ICTN is consistent with previous studies 1,2. To examine the effect of ASIC1KO or amiloride treatment on the inflammatory cell population in EAE, a pre-designed grid (consisting of 4 quadrants each 71 μm×284 μm) was superimposed on images orientated superficially to deep and the number of CD45+CD3− or CD45+CD3+ cells counted. To insure random sampling, 2 quadrants (1 each from dorsal and ventral portions of the cord) were selected from each of 4 images per animal (both quadrants and images were randomly selected) and analyzed. Data are expressed as the mean number of CD45+CD3− or CD45+CD3+ cells per 4×104 □m2 per animal in WT controls, WT-EAE, ASIC1KO EAE and amiloride-treated WT-EAE mice. For analysis of in situ hybridization semi-quantitative microdensitometry was utilized. Images were captured using a Olympus BX60 light microscope with a 40× objective. Digitally captured images were converted to grayscale using ImageJ processing software. The same software was utilized to quantify the optical intensity of in situ hybridization signals in retinal ganglion cell and purkinje cell neurons, which were manually outlined. Background optical intensity was subtracted from all signals under identical conditions for both EAE and control images (n=3-4 per group).

Microglia EOC20 cells, derived from C3H/HeJ CH-2k mice (ATCC)3 were grown as recommended using DMEM media supplemented with 1 mM sodium pyruvate, 10% FCS and 20% LADMAC (ATCC) conditioned media. EOC20 cells were stimulated in the absence or presence of 100 μM amiloride with LPS (200 ng/ml) or interferon-□ (200 U/ml) for 48 h and FACS stained for the respective surface markers and gated on the living cells by using BD Viaprobe (Becton Dickinson).

Statistics

All values are expressed as mean±s.e.m. Where indicated, analyses of significance were performed using the two-tailed Student's t-test for two groups, or ANOVA with post-hoc multiple comparison analysis for multiple groups, or Fishers exact test with P<0.05 (*) considered significant and P<0.001 (**) considered highly significant (Excel, Microsoft and Graph Pad Prism).

All of the experiments described herein have been approved by the local ethics committee and have been licensed under the Animals Scientific Procedures Act of the UK Home Office.

Results $ASIC1^{KO}$-EAE Mice

To study the contribution of ASIC1 to the pathogenesis of EAE, a T cell-dependent mouse model of MS, we used both wild-type C57BL/6 mice (WT-EAE), and C57BL/6 mice with either one (ASIC1HET-EAE) or two copies ($ASIC1^{KO}$-EAE) of a genetically inactivated accn2 (ASIC1) gene. We immunized these mice with amino acid residues 35-55 of myelin oligodendrocyte glycoprotein (MOG35-55), which is known to induce EAE in C57BL/6 mice.

The heterozygous group of ASIC knock out mice (shown in FIG. 1A as triangles) demonstrated similar clinical and neurological deficits to those shown by the C57BL/6 group of mice. By contrast, the homozygous group of ASIC knock out mice (shown in FIG. 1A as squares) demonstrated a reduction in the clinical and neurological deficits observed. $ASIC1^{KO}$-EAE mice had both significantly reduced maximum clinical disease severity (P<0.001) and ensuing clinical deficit (P<0.001) compared to WT-EAE and $ASIC1^{HET}$-EAE mice (FIG. 1A and Table 1).

Adoptive Transfer of MOG35-55-Specific Effector T Cells

To see whether the disease-modifying effect of inactivating ASIC1 was immune-related, we adoptively transferred MOG35-55-specific effector T cells isolated from WT or $ASIC1^{KO}$ mice into naïve WT or $ASIC1^{KO}$ mice. T cells isolated from either group initiated a similar clinical deficit after transfer into WT mice. By contrast, the disease course in $ASIC1^{KO}$ mice receiving MOG-specific T cells from either WT or $ASIC1^{KO}$ donors was equally ameliorated (FIG. 1B). This finding provides indication that the disease-modifying effect of inactivated ASIC1 is independent of any effect on T cells and likely related to ASIC1 expression in the CNS.

pH of Inflamed Spinal Cords

Figure 2:
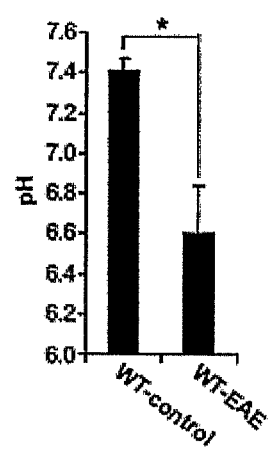
FIG. 2 shows acidosis in spinal cord tissue directly measured in vivo by a micro-pH meter from either un-immunized anesthetized C57BL/6 mice (n=4) or of day 15 post MOG35-55-immunized C57BL/6 mice (n=4). Spinal cords of EAE mice show a marked decrease in tissue pH compared to WT mice (results are presented as mean±s.e.m, * P<0.005).

As ASIC1 fluxes cations in response to a lowering of pH with a half-maximum activation at pH 6.8 for ASIC1a and pH 6.2 for ASIC1b[13], we investigated whether inflamed spinal cords show a lowering in pH. Using a micro-pH meter placed in inflamed spinal cords, we found reduced tissue pH in WT-EAE mice (pH 6.60±0.23) compared to WT-control mice (pH 7.41±0.06; P<0.005) at day 15 post-immunization (p.i.) (FIG. 2). This low pH is compatible with activating ASIC1 and subsequent ion influx in axons in inflammatory lesions in EAE. This acidosis is likely to be a consequence of an inflammation-induced energy failure and a state of 'hypoxia' in axons. Indeed, hypoxia-inducible factor-1α (HIF-1α) was up-regulated in the spinal cord of WT-EAE and $ASIC1^{KO}$-EAE animals compared to WT-control mice, supporting the existence of energy failure in EAE lesions, and consistent with the demonstration of HIF-1α in active MS lesions[14].

ASIC1a Expression

Figure 4:
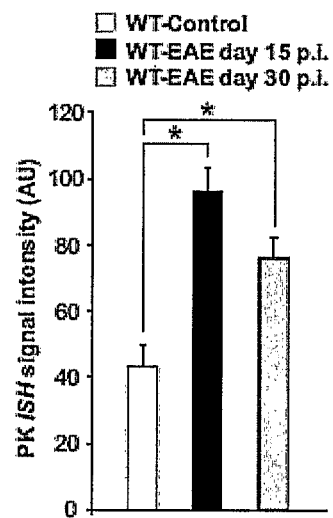
FIG. 4 shows quantification of in situ hybridization signal intensity with a specific ASIC1 probe or ASIC1 sense probe (negative control) in retinal ganglion cells (RGC) of un-immunized WT mice and mice with EAE 15 or 30 days p.i. given in arbitrary units (AU) in cerebellar purkinje cells (PK).

As it has been shown that ASIC1a expression is induced by pro-inflammatory mediators, such as interleukin-1β[15], which is regarded as a crucial cytokine for neuronal damage in several models of neurodegeneration[16] and is up-regulated in CNS inflammatory disease[17] we asked whether inflammation in EAE leads to a quantitative change in ASIC1 expression. The available anti-ASIC1 antibodies gave unreliable staining so we measured ASIC1 expression by quantifying mRNA in neuronal cell bodies in the retina and cerebellum, from which vulnerable axons are derived. ASIC1 mRNA was significantly (P=0.001) up-regulated in inflamed retinal ganglion cells at day 15 p.i, and showed a trend towards higher expression at day 30 p.i., in EAE-mice compared to cells from un-immunized mice; cerebellar Purkinje cells in inflamed lesions showed significant ASIC1 mRNA up-regulation both at day 15 (P=0.002) and day 30 p.i. (P=0.01) (FIGS. 3 and 4).

Taken together these data demonstrate that there is hypoxia and acidosis in inflammatory EAE lesions, associated with an increase in ASIC1 mRNA expression. Together these would combine to increase ASIC1 activity with flux of injurious cations into vulnerable axons.

Optic Nerve/Retinal Explants from WT or $ASIC1^{KO}$ Mice

Figure 5:
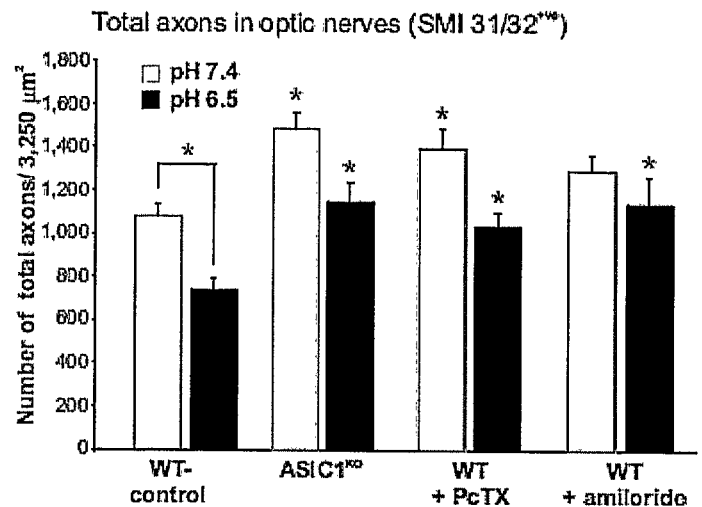
FIG. 5 shows a histogram of total number of axons compared to WT-controls ini optic nerve and retina from WT-control, ASIC1$^{KO}$, WT plus PcTx (100 ng/ml) and WT plus amiloride (100 mM) incubated (18 hours) at pH of 7.4 or 6.5. Asterisks indicate statistical significance in comparison with WT-controls, except the comparison between pH 7.4 and 6.5 within WT-control animals.
Figure 6:
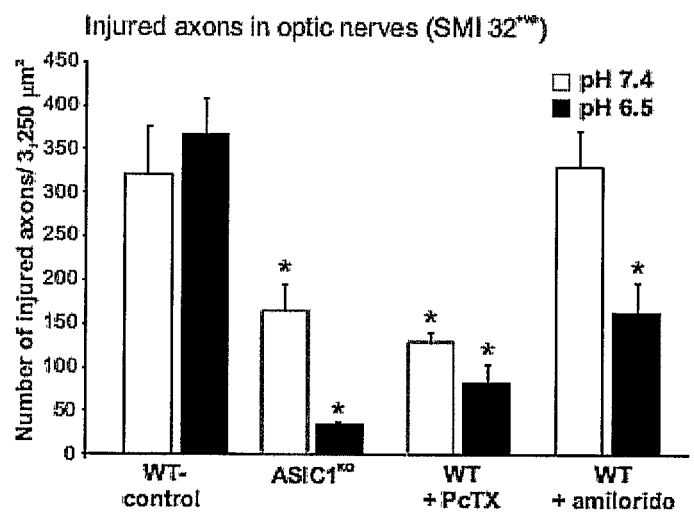
FIG. 6 shows a histogram of the number of injured axons compared to WT-controls ini optic nerve and retina from WT-control, ASIC1$^{KO}$, WT plus PcTx (100 ng/ml) and WT plus amiloride (100 mM) incubated (18 hours) at pH of 7.4 or 6.5. Asterisks indicate statistical significance in comparison with WT-controls, except the comparison between pH 7.4 and 6.5 within WT-control animals.

To evaluate directly the potential deleterious effect of acidosis on axonal integrity and investigate the involvement of ASIC1a, we used an ex vivo model of optic nerve/retinal explants isolated from WT or $ASIC1^{KO}$ mice. We incubated the explants at pH 7.4 or 6.5 in the presence or absence of psalmotoxin 1 (PcTx), a highly specific ASIC1a blocker[18] and measured both the total number of axons (FIG. 5), and the number of axons expressing non-phosphorylated neurofilament as a marker of demyelinated or injured axons[19] (FIG. 6).

Interestingly, loss of axons (FIG. 5) and injured axons (FIG. 6) in the pH 7.4 WT explants, which occurred during the first few hours of culture, was not found in the $ASIC1^{KO}$ derived nerves and was prevented by treatment of WT nerves with PcTx. At pH 6.5 there was a significant loss of axons and more injured axons in WT explants as compared to pH 7.4 with striking preservation in $ASIC1^{KO}$ and PcTx-treated cultures (FIGS. 5 and 6 and Table 2).

In summary, there was a minor neuroprotective effect of $ASIC1^{KO}$ and PcTx treatment at pH 7.4; this could be explained by a reduction in extracellular tissue pH in vitro due to localized tissue hypoxia or axonal injury which may activate ASIC1a through alternate ligands[20] at physiological pH. However, the more extensive neuroprotective effect seen in $ASIC1^{KO}$ tissue and in WT tissue treated with PcTx at pH 6.5 indicates the role of ASIC1, specifically the PcTx-sensitive ASIC1a, in acidosis-related axonal injury in EAE.

Effect of Amiloride

Having established the importance of ASIC1 in axonal degeneration associated with neuroinflammation, we looked for an ASIC1 antagonist with a potential for a cost effective and rapid translation into a clinical setting as a neuroprotective therapy in MS[21]. This is of particular importance as axonal degeneration correlates with clinical deficits and targeting this component might be able to slow or stop the development of further deficits in MS. We identified amiloride, an ASIC blocker, which is a licensed drug used to treat hypertension and congestive heart failure. The advantage of amiloride is that it is easy to administrate and has a proven safety profile. We examined amiloride's influence on acidosis-induced axonal injury in our ex vivo and in vivo models as well as its modifying effect on the clinical disease manifestations in EAE.

Effect of Amiloride on Optic Nerve/Retinal Explants

Interestingly, amiloride resulted in inhibition of axonal injury at pH 6.5 in optic nerve/retinal explants, similar to that found with PcTx treatment or in explants of $ASIC1^{KO}$ mice (FIGS. 5 & 6). However, we observed no neuroprotection at pH 7.4. This difference may relate to the pH dependence of the active moiety of amiloride requiring protonation[22] in contrast to the pH-independent action of PcTx. Therefore, amiloride may be particularly suitable for use in patients since it is only able to inhibit ASICs in tissues where the pH significantly drops, i.e. in pathological conditions such as CNS inflammation.

30 Day Study using Amiloride 6-10 week old female and male C57BL/6 mice were immunized subcutaneously as described above. The mice were sex matched among the different groups. One group of mice were treated with 5 mg/kg body weight (e.g. 100 μg for 20 g mouse) amiloride (Sigma-Aldrich), administered in 100 μl daily starting 5 days after immunization. Another group of mice were treated intraperitoneally with PBS (vehicle) alone to act as the control group. The mice were then monitored for clinical and neurological deficits and each day were assigned a score in accordance with the following classification:

0=healthy;
1=weak tail;
2=tail paralysis;
3=weak/moderate waddling gait with hindlimb paresis;
4=intense waddling gait with hindlimb paresis;
5=full paralysis of the hind or forelimbs;
6=tetraparesis;
7=tetraparalysis; and
8=moribund or death.

Figure 7:
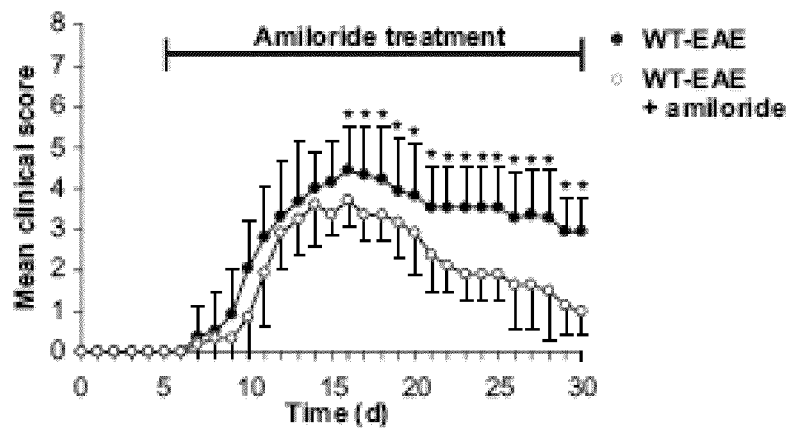
FIG. 7 shows that amiloride treatment ameliorates disease severity and axonal loss in EAE mice.
Figure 7:
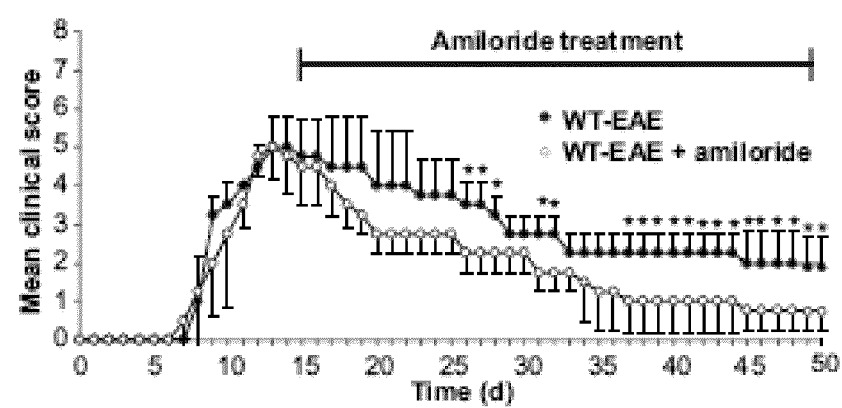
Figure 7:
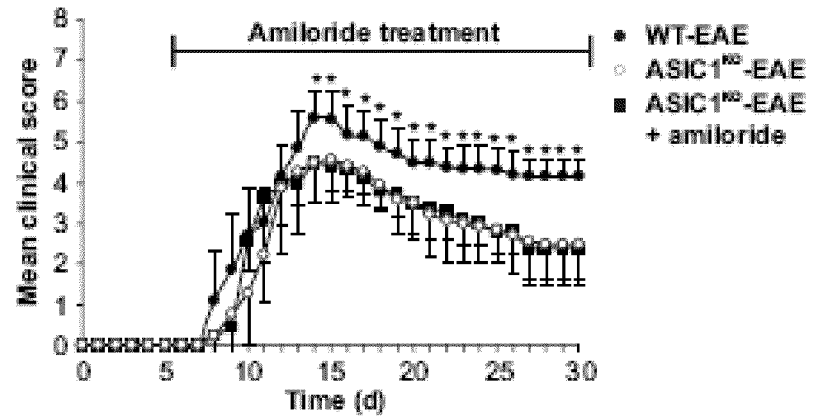

The results of this study can be observed in FIG. 7 wherein the control group (shown by dark, filled circles) simulate the typical onset of multiple sclerosis following immunisation. The two phases of multiple sclerosis can be observed in the results shown in FIG. 7A, for example, the acute, inflammatory phase occurs up until around day 15-18 after which the chronic, neurodegeneration phase occurs. The group of mice treated with amiloride (the open circles) can be clearly seen to demonstrate a reduced mean clinical score when compared with the control group. These results demonstrate the apparent clinical benefits of amiloride in reducing the clinical and neurological deficits associated with multiple sclerosis.

50 Day Clinical Study using Amiloride

This experiment was performed as described above with the exception that the clinical and neurological deficits were observed for an additional 30 days. The results of this study can be seen in FIG. 7B. For the first 20 days of this study, the results are consistent with those obtained in the 30 day study shown in FIG. 1. The key distinction between the results in FIG. 7A and FIG. 7B are observed during the chronic, neurodegenerative phase. For example, amiloride appears to a greater extent during the chronic, neurodegenerative phase than during the acute, inflammatory phase. These results demonstrate the likely neuroprotective effect of amiloride, in particular during the chronic, neurodegenerative phase of multiple sclerosis.

Strikingly, the results of these studies show a reduction in maximum clinical disease severity ($P<0.001$) as well as an effect on subsequent clinical deficit ($P<0.001$) in WT-EAE mice treated daily with amiloride from day 5 p.i. compared to PBS-treated WT-EAE mice (FIG. 7A and Table 1). Importantly, treatment started at the peak of disease, day 15 p.i., was almost equally effective in reducing the subsequent clinical score (FIG. 7$b$, $P<0.05$). The effect of treatment after disease onset has direct clinical relevance, as patients will start treatment after having experienced their first relapses.

Effect of Amiloride on ASIC1$^{KO}$ Mice

Figure 8:
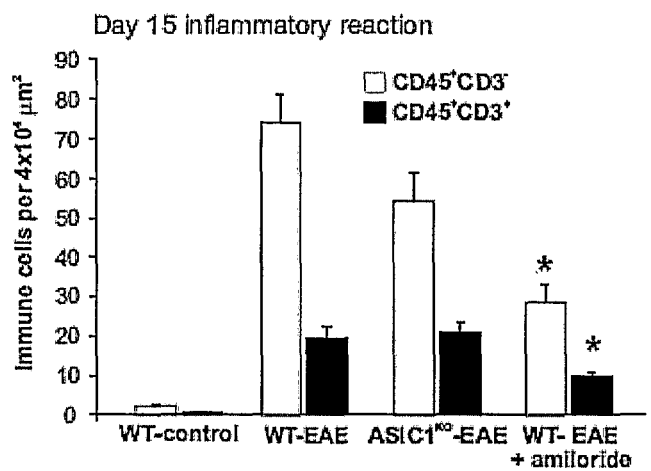
FIG. 8 shows quantification of the number of CD45$^+$CD3$^-$ and CD45$^+$CD3$^+$ cells in 4-6 animals of each group at day 15 p.i. Results are presented as mean±s.e.m, * P<0.05.
Figure 9:
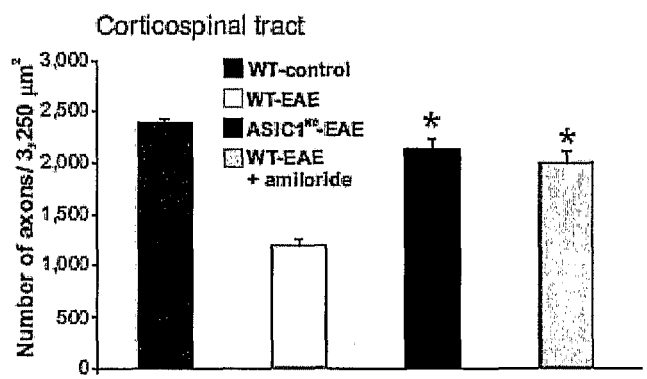
FIG. 9 shows quantification of neurofilament (SMI 31, 32) positive axons in the cortico-spinal tract at day 30 p.i. in WT-control animals, WT-EAE, ASIC 1$^{KO}$-EAE or WT-EAE mice treated with amiloride. Results are from 4-6 animals for each group and presented as mean±s.e.m, * P<0.05.
Figure 10:
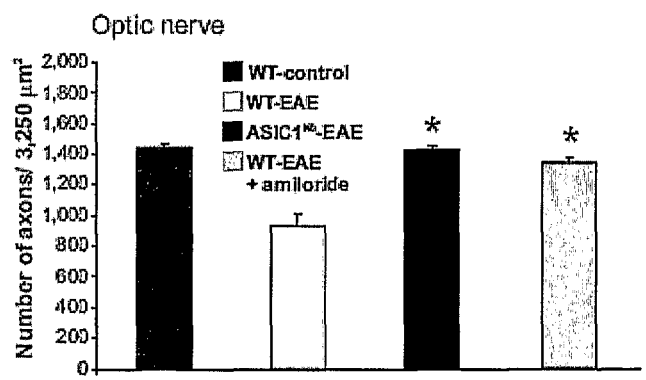
FIG. 10 shows quantification of neurofilament (SMI 31, 32) positive axons in the optic nerve at day 30 p.i. in WT-control animals, WT-EAE, ASIC1$^{KO}$-EAE or WT-EAE mice treated with amiloride. Results are from 4-6 animals for each group and presented as mean±s.e.m, * P<0.05.
Figure 11:
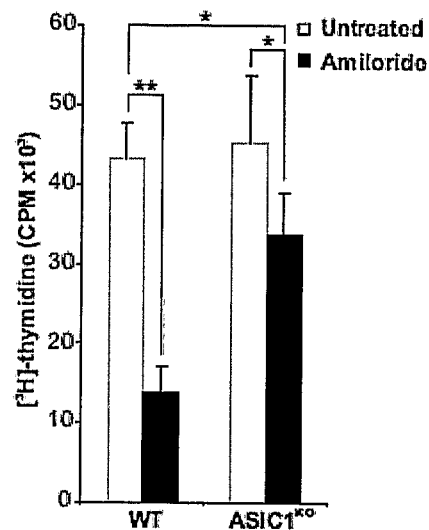
FIG. 11 shows proliferation of T cells measured by [methyl-$^3$H]-thymidine incorporation of WT or ASIC1$^{KO}$ mice 5 d after stimulation with anti-CD3/-CD28 antibodies in the absence or presence of 100 μM amiloride. Results show a representative experiment of three independent experiments.
Figure 12:
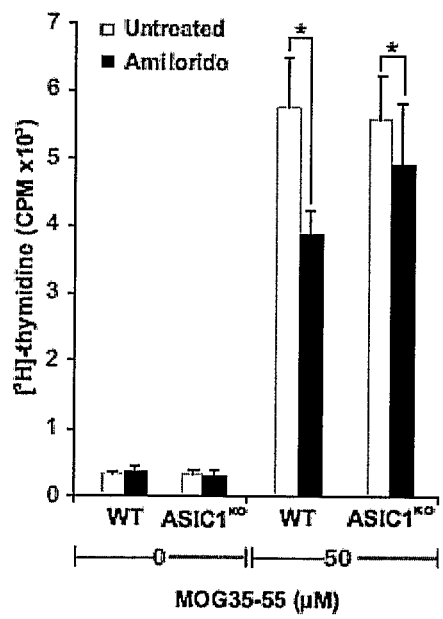
FIG. 12 shows proliferation of T cells measured by [methyl-$^3$H]-thymidine incorporation of WT, ASIC1$^{KO}$ untreated or treated with amiloride (day 3 p.i.) (n=4 per group) were immunized with MOG35-55/CFA and draining lymph nodes were isolated on day 10 after immunization. The cells were re-stimulated in vitro for 4 days with either medium alone or MOG peptide. Proliferation was measured by [methyl-$^3$H]-thymidine incorporation and is represented as a mean±s.e.m counts per minute (cpm) in triplicate.

Since amiloride is a non-specific ASIC blocker[5], it may directly influence other ion channels and transporter systems such as voltage-gated sodium channels and $Na^+$—$Ca^{2+}$ exchangers[23] which have also been implicated in CNS inflammatory axonal damage in EAE and MS[24,25]. To investigate whether amiloride exerts its effects by blocking ASIC1 we immunized ASIC1$^{KO}$ mice and compared the results in the presence or absence of amiloride. Interestingly, amiloride offered no additional clinical benefit compared to untreated ASIC1$^{KO}$-EAE mice (FIG. 7C), indicating that amelioration of EAE by amiloride is likely to be mediated primarily by blockade of ASIC1. However, when we examined the inflammatory infiltrates and axonal numbers, comparing WT-EAE, ASIC1$^{KO}$-EAE and amiloride-treated WT-EAE at day 15 and day 30 p.i, we found a reduction in the inflammatory infiltrates of both CD45$^+$CD3$^-$ (predominantly macrophages/microglia) and CD45$^+$CD3$^+$ cells (T cells) in the spinal cord at day 15 in amiloride-treated WT-EAE mice but not in ASIC1$^{KO}$-EAE mice (FIG. 8). Nevertheless, by day 30 p.i. both ASIC1$^{KO}$-EAE and amiloride-treated WT-EAE mice showed profound axonal preservation within the dorsal corticospinal tract (FIG. 9), dorsal column and optic nerve (FIG. 10) in comparison to WT-EAE mice (all data summarized in Table 3). These data provide indication that targeting ASIC1 is predominantly neuroprotective but that there is an additional immunomodifying effect of amiloride via ion channels other than ASIC1, for instance voltage-gated Na$^+$ channels on T cells[26] or an effect on macropinocytosis and antigen-presentation by macrophages[27].

Figure 13:
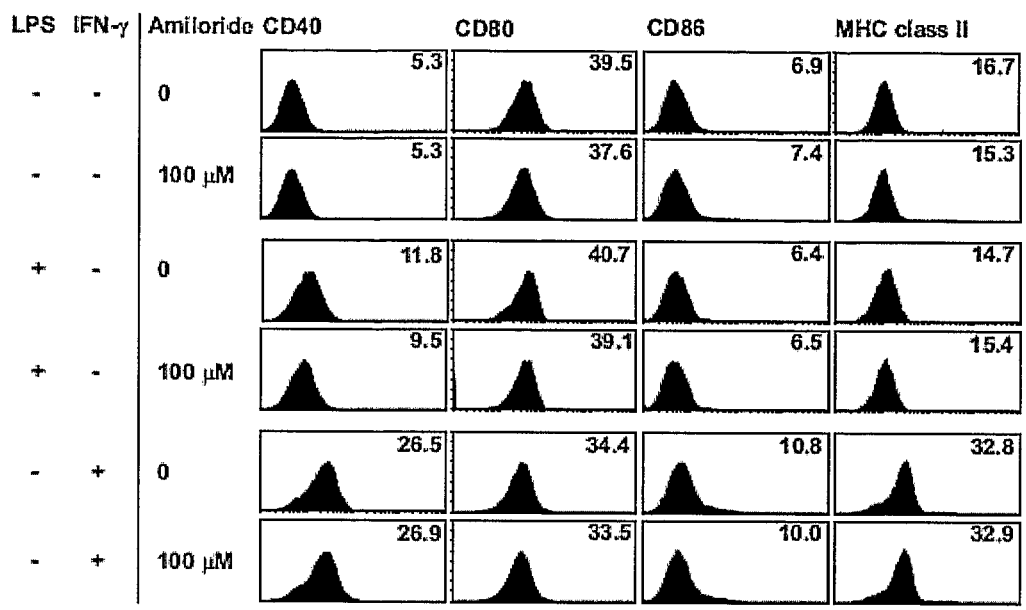
FIG. 13 shows flow cytometric analysis of cell surface molecules (CD40, CD80, CD86 and I-A$^k$ (MHC class II)) on untreated or amiloride-treated EOC20 microglia cells after 48 h incubation with LPS or IFN-γ. Amiloride (100 μM) showed no effect on the upregulation of these cell surface markers. The mean peak fluorescence intensity is given in the respective histograms and represents one of two separate experiments.
Figure 14:
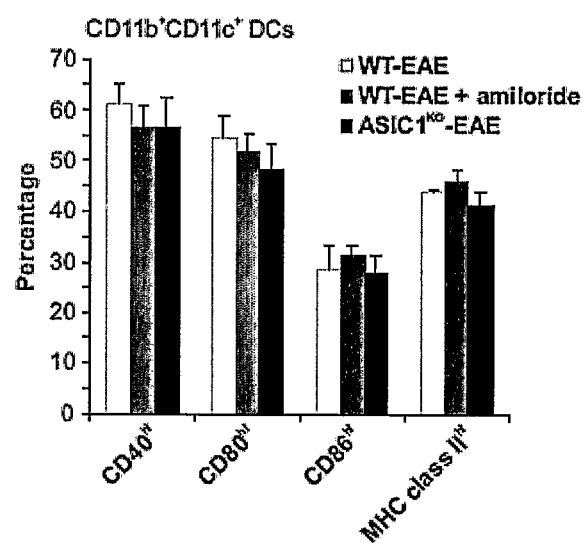
FIG. 14 shows cytometric analysis of draining lymph nodes (n=3 per group) from untreated or amiloride-treated (from day 3 p.i.) MOG35-55 immunized WT or untreated ASIC1$^{KO}$ mice isolated at day 10 p.i. Activation markers CD40, CD80, CD86 and I-A$^k$ expression were analyzed on CD11b$^+$CD11c$^+$ dendritic cells. No significant difference could be detected in the percentage of expressing cells.

To clarify the situation we looked directly at the role of ASICs in the immune system. There were no differences in immune cell subsets or distribution between un-immunized ASIC1$^{KO}$ and WT mice (Table 4) nor could we detect an altered antigen-presenting cell (APC) function, as in vitro and in vivo activation markers in APCs were unaffected by amiloride treatment or ASIC1 deletion (FIGS. 13 and 14). ASIC1 mRNA was detected in T and B cells, but absent in macrophages, and only T cells showed expression at the protein level. However, ASIC3 and ASIC4 mRNAs were found in T cells, macrophages and B cells providing indication of a possible role for other ASICs and a potential target for amiloride. Comparable non-specifically-stimulated (anti-CD3/-CD28) proliferation profiles were found between splenic T cells from un-immunized WT and ASIC1$^{KO}$ mice although amiloride inhibited T cell proliferation in WT mice ($P<0.001$) with only a limited effect on ASIC1$^{KO}$ T cells (FIG. 13). There was also some reduction in antigen-specific (MOG)-induced T cell proliferation in draining lymph node cells from amiloride-treated WT-EAE mice ($P<0.05$), with less effect on T cells from ASIC1$^{KO}$ mice (FIG. 14). These observations provide indication that ASIC1 has a modest role in T cell function which is blocked by amiloride, but that there are other amiloride-sensitive ion channels (possibly ASIC3, ASIC4 and voltage-gated Na$^+$-channels[26]) that may partly determine the immunosuppressive effect of the drug. However, it appears that the ASIC1 deletion in T cells is altogether compensated as they show no significant difference in proliferation to their WT counterparts, which was corroborated by the adoptive transfer experiments (FIG. 1B). In addition, as amiloride treatment of ASIC1$^{KO}$ delivers no additional clinical benefit (FIG. 7C), implies that the immunosuppressive effect is mild and the main determinant of neuroprotection is the block of ASIC1 channels in the CNS. Thus amiloride treatment would be unlikely to run the risk of unexpected opportunistic infections as occur with some immunosuppressive treatments[21].

Figure 15:
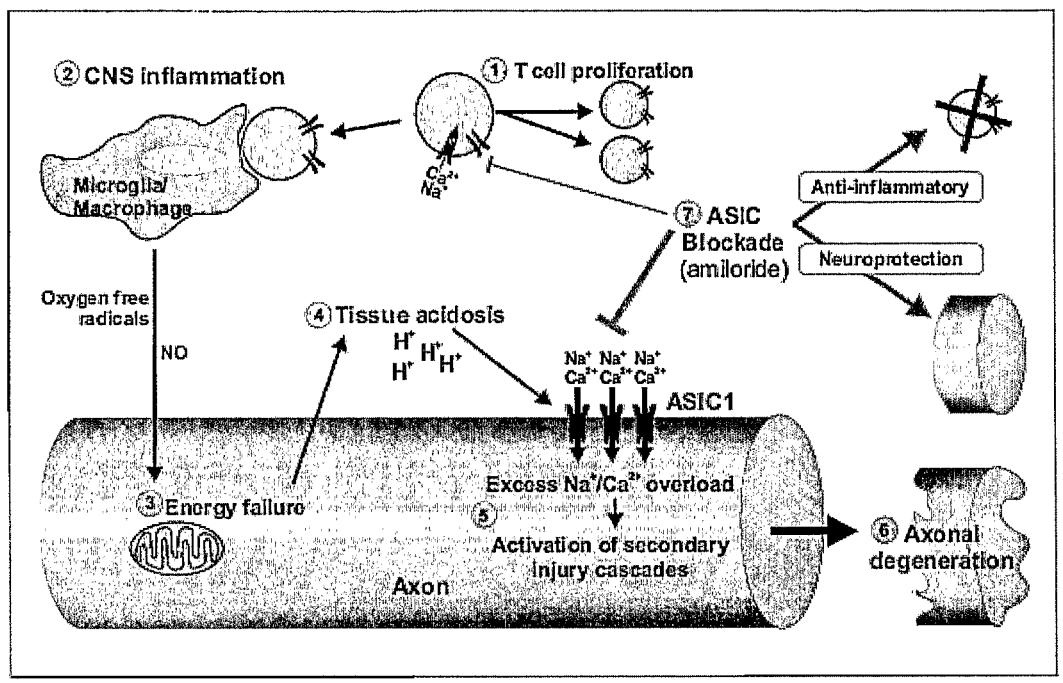
FIG. 15 shows a schematic demonstration of the mechanism of action for ASIC1 in CNS inflammatory disease and axonal degeneration. (1) ASIC1 and other amiloride-sensitive ion channels play a role in T cell activation and proliferation increasing the population of auto-reactive T cells within the CNS and driving the inflammatory response. (2) Autoimmune CNS inflammation then initiates a cascade with subsequent release of toxic mediators, including nitric oxide and oxygen free radicals. (3) Energy failure ensues due to nitric oxide induced mitochondrial dysfunction causing (4) tissue acidosis. The increased concentration of protons (acidosis) leads to activation of ASIC1 expressed along axons. (5) Opening of ASIC1 expressed in axons leads to influx and accumulation of injurious Na$^+$ and Ca$^{2+}$ ions. Activation of secondary injury cascades, such as proteases, causes breakdown of the axonal cytoskeleton leading to (6) axonal degeneration and development of non-remitting clinical deficits. (7) Pharmacological blockade of ASIC by amiloride acts through both neuroprotective and anti-inflammatory mechanisms with potential for amelioration of CNS inflammatory disease.

Using both gene deletion and pharmacological approaches in combination with functional (in vivo and in vitro) and neuropathological studies we have delineated a novel mechanism involving acidosis-mediated axonal damage in CNS inflammation (diagrammatically represented in FIG. 15), and shown that the licensed, clinically safe and relatively cheap drug amiloride significantly reduces axonal damage in EAE, principally by acting on ASIC1. Together with its potential to provide some mild immunosuppression, which might contribute in a clinical setting, ASIC1 represents an attractive novel target for MS therapy.

TABLE 1

| Mouse genotype | Treatment | Incidence | Day of disease onset[a] | Maximum clinical score[a] | Clinical score at day 30 p.i.[a] |
|---|---|---|---|---|---|
| C57BL/6 WT-EAE | PBS day 5 p.i. or none | 52/59 (88%) | 9.65 ± 2.15 | 5.36 ± 0.92 | 3.45 ± 0.89 |
| C57BL/6 ASIC1$^{KO}$-EAE | None | 22/25 (88%) | 9.35 ± 1.58 | 4.39 ± 1.13 (P = 0.0009) | 1.81 ± 1.07 (P = 0.0001) |

TABLE 1-continued

| Mouse genotype | Treatment | Incidence | Day of disease onset[a] | Maximum clinical score[a] | Clinical score at day 30 p.i.[a] |
|---|---|---|---|---|---|
| C57BL/6 WT-EAE | Amiloride day 5 p.i. | 38/44 (86%) | 10.92 ± 3.03 (P = 0.031) | 4.37 ± 0.96 (P = 0.000005) | 1.50 ± 0.74 (P = 2.35 × 10$^{-11}$) |

[a]Results are presented as mean ± s.e.m and represent pooled data of at least three independent experiments. P value refers to an ANOVA test with Bonferroni post-test in comparison with untreated C57BL/6 WT-EAE.

TABLE 2

| | Total axons/3,250 µm$^2$ (SMI 31/32)[a] | | Injured axons/3,250 µm$^2$ (SMI 32)[a] | | Injured axons % of total | |
|---|---|---|---|---|---|---|
| | pH 7.4 | pH 6.5 | pH 7.4 | pH 6.5 | pH 7.4 | pH 6.5 |
| C57BL/6 WT | 1,081.0 ± 52.5 | 741.8 ± 51.5 (P = 0.002)[b] | 320.5 ± 56.0 | 366.5 ± 71.3 | 29.6 | 49.4 |
| C57BL/6 ASIC1$^{KO}$ | 1,484.2 ± 70.9 (P = 0.002) | 1,148.6 ± 85.6 (P = 0.006) | 164.4 ± 31.0 (P = 0.04) | 34.6 ± 3.3 (P = 0.01) | 11.0 | 3.0 |
| C57BL/6 WT + PcTx | 1,395.7 ± 87.6 (P = 0.02) | 1,036.0 ± 61.5 (P = 0.01) | 129.0 ± 11.7 (P = 0.02) | 81.5 ± 21.6 (P = 0.01) | 9.3 | 7.9 |
| C57BL/6 WT + amiloride | 1,291.8 ± 72.1 (P = 0.06) | 1,138.4 ± 125.0 (P = 0.04) | 329.7 ± 40.5 (P = 0.9) | 162 ± 34.9 (P = 0.04) | 25.4 | 14.2 |

[a]Results are presented as mean ± s.e.m of 4-5 optic nerves per group
[b]Compared to pH 7.4 WT

TABLE 3

| | Number of neurofilament (SMI 31, 32) positive axons/3,250 µm$^2$ | | | Number of CD45$^+$CD3$^-$ cells/4,000 µm$^2$ spinal cord (dorsal and ventral columns) | | Number of CD45$^+$CD3$^+$ cells/4,000 µm$^2$ spinal cord (dorsal and ventral columns) |
|---|---|---|---|---|---|---|
| | Cortico-spinal tract[a] | Dorsal column[a] | Optic nerve[a] | Day 15 post immunisation[a] | Day 30 post immunisation[a] | Day 15 post immunisation[a] |
| C57BL/6 WT | 2,395.0 ± 38.1 | 458.4 ± 7.4 | 1,443.7 ± 23.9 | 2.3 ± 0.3 | | 0.6 ± 0.1 |
| C57BL/6 WT-EAE[b] | 1,198.3 ± 66.9 (P = 0.000004) | 195.5 ± 2.5 (P = 0.000005) | 933.4 ± 69.7 (P = 0.0005) | 74 ± 6.8 (P = 0.0001) | 36.5 ± 5.9 (P = 0.01) | 19.4 ± 3.0 (P = 0.002) |
| C57BL/6 ASIC1$^{KO}$-EAE[c] | 2,139.2 ± 96.8 (P = 0.0003) | 356.6 ± 31.1 (P = 0.007) | 1,424.1 ± 27.7 (P = 0.002) | 54.1 ± 7.1 (P = 0.07) | 10.9 ± 5.2 (P = 0.02) | 20.7 ± 2.7 (P = 0.8) |
| C57BL/6 WT-EAE + amiloride[c] | 2,003.5 ± 108.7 (P = 0.001) | 294.1 ± 26.3 (P = 0.02) | 1,339.9 ± 37.9 (P = 0.002) | 28.5 ± 4.4 (P = 0.0005) | 8.75 ± 2.17 (P = 0.01) | 9.8 ± 1.1 (P = 0.02) |

[a]Results are presented as mean ± s.e.m of 4-6 animals per group.
[b]Data compared to WT
[c]Data compared to WT-EAE

TABLE 4

| Organ | Gate | Cell type | WT (%)[a] | ASIC1$^{KO}$ (%)[a] |
|---|---|---|---|---|
| Spleen | CD3+CD4+ | CD4+ T cells | 22.2 ± 0.9 | 21.9 ± 0.7 |
| | CD3+CD8+ | CD8+ T cells | 15.0 ± 0.4 | 13.8 ± 0.4 |
| | CD3+NK1.1+ | NKT cells | 4.4 ± 2.0 | 3.9 ± 0.4 |
| | CD3-NK1.1+ | NK cells | 5.3 ± 0.2 | 6.0 ± 1.3 |
| | CD19+ | B cells | 59.2 ± 7.3 | 63.6 ± 10.5 |
| | CD11b+CD11c+ | DCs | 8.4 ± 4.1 | 7.0 ± 3.4 |
| | CD11b+CD11c− | Macrophages | 10.1 ± 3.2 | 8.8 ± 2.8 |
| Lymph node | CD3+CD4+ | CD4+ T cells | 33.0 ± 0.6 | 33.9 ± 7.6 |
| | CD3+CD8+ | CD8+ T cells | 23.1 ± 0.2 | 21.5 ± 6.0 |
| | CD3+NK1.1+ | NKT cells | 1.7 ± 0.7 | 1.8 ± 0.9 |
| | CD3-NK1.1+ | NK cells | 1.0 ± 0.1 | 1.2 ± 0.2 |
| | CD19+ | B cells | 32.8 ± 8.6 | 36.7 ± 12.4 |
| | CD11b+CD11c+ | DCs | 2.8 ± 2.3 | 2.7 ± 1.9 |
| | CD11b+CD11c− | Macrophages | 7.2 ± 3.6 | 7.5 ± 3.0 |
| Bone marrow | CD3+CD4+ | CD4+ T cells | 3.3 ± 0.4 | 3.0 ± 0.4 |
| | CD3+CD8+ | CD8+ T cells | 2.6 ± 0.01 | 2.5 ± 0.6 |
| | CD3+NK1.1+ | NKT cells | 3.0 ± 0.8 | 3.1 ± 0.5 |
| | CD3-NK1.1+ | NK cells | 7.4 ± 4.5 | 7.1 ± 3.1 |
| | CD19+ | B cells | 28.2 ± 6.3 | 26.3 ± 9.8 |
| | CD11b+CD11c+ | DCs | 7.4 ± 4.8 | 6.4 ± 2.4 |
| | CD11b+CD11c− | Macrophages | 41.2 ± 8.5 | 40.7 ± 4.5 |
| Thymus | CD4+CD8+ | DP thymocytes | 73.6 ± 3.4 | 65.5 ± 2.0 |
| | CD4+CD8− | SP CD4+ thymocytes | 5.7 ± 4.0 | 6.2 ± 4.6 |

TABLE 4-continued

| Organ | Gate | Cell type | WT (%)[a] | ASIC1[KO] (%)[a] |
|---|---|---|---|---|
| | CD4−CD8+ | SP CD8+ thymocytes | 0.8 ± 0.4 | 0.8 ± 0.5 |

[a]Results are presented as mean ± s.e.m of 3 animals per group.

REFERENCES

1. Lovas, G., et al. *Brain* 123 (Pt 2), 308-17 (2000).
2. Kornek, B. et al. *Am J Pathol* 157, 267-76 (2000).
3. Wemmie, J. A. et al *J Neurosci* 23, 5496-502 (2003).
4. Garcia-Anoveros, J. et al. *Proc Natl Acad Sci USA* 94, 1459-64 (1997).
5. Waldmann, R., et al. *Nature* 386, 173-7 (1997).
6. Alvarez de la Rosa, D. et al. *J Physiol* 546, 77-87 (2003).
7. Stys, P. K. & Lopachin, R. M. *Neuroscience* 82, 21-32 (1998).
8. Waxman, S. G. *Trends Mol Med* 12, 192-5 (2006).
9. Stys, P. K. *J Neurol Sci* 233, 3-13 (2005).
10. Wemmie, J. A., et al. *Trends Neurosci* (2006).
11. Zha, X. M. et al *Proc Natl Acad Sci USA* 103, 16556-61 (2006).
12. Xiong, Z. G. et al. *Cell* 118, 687-98 (2004).
13. Benson, C. J. et al. *Proc Natl Acad Sci USA* 99, 2338-43 (2002).
14. Aboul-Enein, F. et al. *J Neuropathol Exp Neurol* 62, 25-33 (2003).
15. Mamet, J. et al. *J Neurosci* 22, 10662-70 (2002).
16. Allan, S. M., Tyrrell, P. J. & Rothwell, N. J. *Nat Rev Immunol* 5, 629-40 (2005).
17. Cannella, B. & Raine, C. S. *Ann Neurol* 37, 424-35 (1995).
18. Escoubas, P. et al. *J Biol Chem* 275, 25116-21 (2000).
19. Trapp, B. D. et al. *N Engl J Med* 338, 278-85 (1998).
20. Lingueglia, E. et al *Peptides* 27, 1138-52 (2006).
21. Feldmann, M. & Steinman, L. *Nature* 435, 612-9 (2005).
22. Benos, D. J. et al *J Gen Physiol* 68, 43-63 (1976).
23. Kleyman, T. R. & Cragoe, E. J., Jr. *J Membr Biol* 105, 1-21 (1988).
24. Craner, M. J. et al E. *Brain* 127, 294-303 (2004).
25. Craner, M. J. et al. *Proc Natl Acad Sci USA* 101, 8168-73 (2004).
26. Lai, Z. F. et al. *J Immunol* 165, 83-90 (2000).
27. Norbury, C. C. et al. *Immunity* 3, 783-91 (1995).
28. Wemmie, J. A. et al. *Neuron* 34, 463-77 (2002).
29. Gregersen, J. W. et al. *Nature* 443, 574-7 (2006).
30. Craner, M. J. et al. *J Neuropathol Exp Neurol* 62, 968-75 (2003).
31. Hsu, J. Y. et al. *Brain Res* 1084, 16-27 (2006).
32. Jeon, C. J., Strettoi, E. & Masland, R. H. *J Neurosci* 18, 8936-46 (1998).
33. Walker, W. S. et al. *J Neuroimmunol* 63, 163-74 (1995).

The invention claimed is:

1. A method of reducing axonal degeneration in an individual having multiple sclerosis, comprising administering an ASIC1 receptor antagonist to the individual, wherein the ASIC1 antagonist comprises 3,5-diamino-N-(aminoiminomethyl)-6-chloropyrazinecarboxamide or a pharmaceutically acceptable salt or solvate thereof.

2. The method of claim 1, wherein the multiple sclerosis is the neurodegenerative phase of multiple sclerosis.

3. The method of claim 1, wherein the ASIC1 receptor antagonist is combined with an additional therapeutic agent.

4. The method of claim 3, wherein the additional therapeutic agent is an anti-inflammatory or immunomodulatory agent.

5. The method of claim 1, wherein the ASIC1 antagonist is 3,5-diamino-N-(aminoiminomethyl)-6-chloropyrazinecarboxamide hydrochloride dihydrate.

* * * * *